United States Patent [19]

Khattak

[11] Patent Number: 4,899,296

[45] Date of Patent: Feb. 6, 1990

[54] PAVEMENT DISTRESS SURVEY SYSTEM

[76] Inventor: Anwar S. Khattak, 612 S. Lincoln, Spokane, Wash. 99204

[21] Appl. No.: 229,655

[22] Filed: Aug. 8, 1988

Related U.S. Application Data

[63] Continuation-in-part of Ser. No. 195,321, May 18, 1988, abandoned, Ser. No. 120,066, Nov. 13, 1987, Pat. No. 4,788,859, Ser. No. 144,986, Jan. 19, 1988, abandoned, and Ser. No. 150,955, Feb. 1, 1988.

[51] Int. Cl.$^4$ .............................................. G01B 11/30
[52] U.S. Cl. .................................. 364/550; 364/557; 374/129; 358/108; 73/146
[58] Field of Search ............... 364/551.01, 550, 554, 364/505, 506, 507, 557; 354/81; 358/108, 106, 93; 382/10, 8; 73/146; 356/376; 33/557; 250/560, 563; 374/137, 129

[56] References Cited

U.S. PATENT DOCUMENTS

| | | | |
|---|---|---|---|
| 4,052,712 | 10/1977 | Ohama et al. | 346/107 R |
| 4,251,931 | 2/1981 | McKechnie | 73/146 |
| 4,274,091 | 6/1981 | Decker | 340/583 |
| 4,456,829 | 6/1984 | Fohey | 250/560 |
| 4,539,561 | 9/1985 | Wolff | 340/675 |
| 4,653,316 | 3/1987 | Fukuhara | 73/146 |
| 4,674,327 | 6/1987 | Swindall et al. | 73/146 |
| 4,700,223 | 10/1987 | Shontaro et al. | 358/93 |
| 4,708,472 | 11/1987 | Hofman | 356/2 |
| 4,741,207 | 5/1988 | Spangler | 73/146 |
| 4,781,058 | 11/1988 | Arnberg | 73/84 |
| 4,786,815 | 11/1988 | Walker et al. | 250/560 |
| 4,788,859 | 12/1988 | Khattak | 73/146 |

FOREIGN PATENT DOCUMENTS

| | | | |
|---|---|---|---|
| 0147376 | 11/1980 | Japan | 73/146 |
| 0147377 | 11/1980 | Japan | 73/146 |
| 0163808 | 10/1982 | Japan | 356/376 |
| 0231404 | 12/1984 | Japan | 356/376 |
| 2977822 | 12/1981 | United Kingdom | 73/146 |

Primary Examiner—Parshotam S. Lall
Assistant Examiner—S. A. Melnick
Attorney, Agent, or Firm—Wegner & Bretschneider

[57] ABSTRACT

A pavement inspection apparatus is described for inspecting the condition of a full lane of pavement using a vehicle capable of traveling along the lane at normal traffic speeds, such as 55 miles per hour. The apparatus is capable of determining the size and shapes of surface distress features such as longitudinal cracks, transverse cracks, alligator cracks, design joints, and potholes. The apparatus has two video array cameras that project downward onto the pavement with overlapping fields of view for generating X-Y pixel data from at least a 12-foot lane width of highway pavement as the vehicle moves over the pavement. The cameras are mounted at acute angles with respect to each other. The apparatus includes distress feature analysis electronics for determining the size, shape and location of surface distress features and evaluates such features against preset standard values to determine the severity of the determined features. Additionally, the apparatus has infrared cameras for subsurface exploration. Subsurface pavement features, such as, the soil type and moisture content distribution are determined by the distortions in the surface temperature profile captured by the infrared cameras.

9 Claims, 13 Drawing Sheets

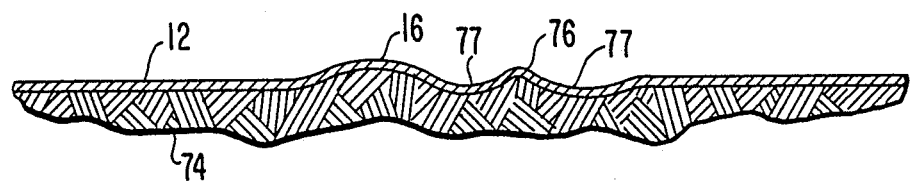
FIG. 7
FIG. 8
FIG. 9
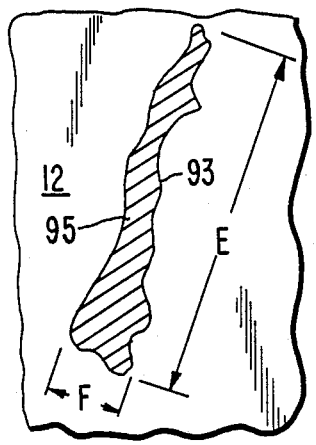
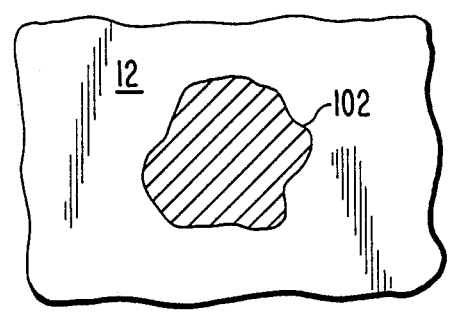
FIG. 10
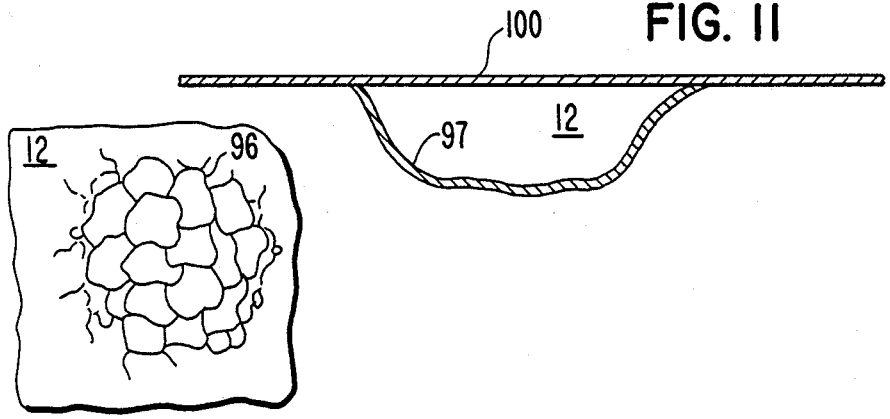
FIG. 11
FIG. 12          FIG. 13
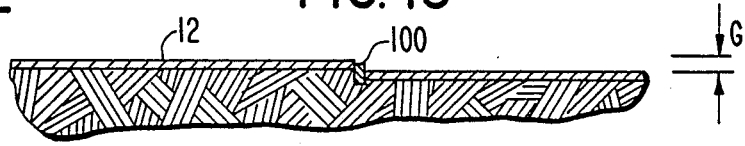

PAVEMENT DISTRESS SURVEY SYSTEM

This application is a continuation-in-part of application Ser. No. 195,321, filed May 18, 1988 now abandoned; application Ser. No. 120,066, filed Nov. 13, 1987, now U.S. Pat. No. 4,788,859; application Ser. No. 144,986, filed Jan. 19, 1988, now abandoned; and application Ser. No. 150,955, filed Feb. 1, 1988, the later three applications all being incorporated herein by reference.

BACKGROUND OF THE INVENTION

Pavement in the form of city streets, county roads, airports, state and interstate highways, is one of the most critical elements of a nation's infrastructure. Managing the serviceability of this critical public resource involves obtaining an accurate measurement of the condition of the pavement and relating such conditions to other critical information such as traffic, climate and design information so that current and future needs can be determined and effective maintenance and reconstruction programs can be formulated.

Fundamental to an effective maintenance and reconstruction program is obtaining of very accurate information concerning the condition of the pavement. At the present such procedures for obtaining information are very time consuming and labor intensive and are inherently inaccurate and unreliable. Despite the expenditure of large amounts of sums, major reconstruction appropriations are often founded upon very inaccurate assessments of the pavement condition and the condition of the subgrade and foundation beneath the pavement.

Despite a number of attempts that have been made to develop equipment for testing the condition of the pavement, most public agencies have utilized a manual system of analyzing the condition of the pavement by the human eye by directly viewing the pavement surface or indirectly viewing the pavement through the use of photographs that have been taken of the pavement. In the later process, the photos are analyzed by the human eye to determine the presence and severity of pavement distress features. U.S. Pat. No. 3,151,235 granted Sept. 29, 1964 to Greenshields is an example.

In a somewhat similar context, mobile equipment has been devised in the past for determining the roughness of the road or pavement. Examples of such mobile equipment are illustrated in U.S. Pat. No. 3,983,746 granted to Ross A. Phillips et al. on Oct. 5, 1976 and U.S. Pat. No. 4,422,322 granted to Elson B. Spangler on Dec. 27, 1983.

More recently Highway Products International, Inc. of Paris, Ontario, Canada has developed a "automatic road analyzer" that has a van having a piezo resistant accelerometer mounted on the rear axle for measuring the longitudinal profile of a lane of pavement. It also has a front sensor bumper bar that is seven feet long with fold-up wing-type extensions that extend out to a full lane width of twelve feet. The sensor bar has ultrasonic transducers mounted on twelve inch centers across the bumper for measuring the transverse profile of the road as the van moves down the lane. Rather than taking photographs of the surface of the roadways, the Highway Products International, Inc. equipment also utilizes video cameras for continuously capturing an oblique view of the right-of-way pavement surface that may be visually inspected and kept for retrieval purposes. It should be noted that to cover a full twelve feet lane width the Highway Products International, Inc. equipment requires the implementation of special wide load traffic control procedures because the equipment extends outwardly to a width of twelve feet (wide load). It is very difficult to utilize such equipment during normal hours on a highway or to operate the equipment at the normal traffic speed such as fifty-five miles per hour.

Another company—Earth Technology Corporation, through its Pavement Condition Evaluation Services of Sparks, Nevada, is experimenting with placing three linear slit video scanning cameras either along the front bumper or along the back bumper of a van as the van moves over the pavement for scanning one pixel line at a time to develop information concerning the longitudinal and transverse profile of the pavement and to identify the presence and severity of surface distress features. Although Earth Technology Corporation hopes to be able to operate such a system at normal traffic speeds, at the present time it appears unable to do so.

It has been recognized for many, many years that the layered system reaction modulus and hence the condition of the subgrade and base may be evaluated by measuring the deflection of the pavement with respect to a known applied load in which the load may be stationary or mobile. Several attempts have been made to provide equipment for determining pavement deflection. One such device is shown in U.S. Pat. No. 4,406,823 granted to Jean-Claude Gressin on Oct. 18, 1983. An earlier effort along this line is shown in U.S. Pat. No. 27,875 granted to G. Swift on Jan. 8, 1974. U.S. Pat. No. 3,888,108 granted to Frank Brands on June 10, 1975 is concerned with measuring of an energy pulse through the pavement as an indicator of its structural strength.

Moreover, reinforced concrete and asphalt pavements absorb the sun's heat during the day and gives off thermal radiation at night. The pavement surface radiation pattern is closely related to the subsurface physical conditions, such as the type of soil, moisture distribution, or the like. Any variation in the subsurface conditions distort the heat emission pattern of the pavement surface. The heat pattern variation therefore can be related to changes taking place under the pavement in response to the variation in the weather conditions or the immediate environment surrounding a section of the pavement.

In order to conduct such a subsurface exploration of the pavement, the use of infra-red cameras are used to capture the pavement surface temperature profile at night from a surveillance vehicle. The pavement or field heat distortion patterns obtained by the infra-red cameras are interpreted by comparing them to a set of known and/or standard temperature profiles, either laboratory developed or measured, of a best-fit basis or analysis. The standard or known thermal patters are obtained from, for example, laboratory tests or experiments on laboratory-manufactured concrete, asphalt slabs, concrete slabs, or the like, supported on a variation of known soil layers having known moisture content distribution substantially representing field conditions.

An object of this invention is to provide pavement inspection equipment that includes a mobile vehicle such as a van that does not require the use of any special traffic procedures and that can be utilized at all hours of the day without disrupting or detouring or slowing normal traffic.

A still further object of this invention is to provide pavement inspection equipment that is capable of obtaining very reliable and accurate information concerning not only the longitudinal and transverse profile of the pavement, but identification and classification of pavement distress features such as cracks, potholes, slab displacements, and pavement separations.

A still further object of this invention is to provide a novel pavement inspection equipment which is also capable of efficiently carrying out pavement sub-surface inspection or exploration for information on types of base and/or sub-grade soils and moisture content distribution thereof.

A still further object of this invention is to provide unique pavement inspection equipment that is capable of obtaining very accurate information concerning the condition of the pavement at a very low per mile inspection cost that is in a summarized and usable form that can be readily utilized by those persons who are responsible for pavement maintenance and servicing.

These and other objects and advantages of this invention will become apparent upon reading the following detailed description of a preferred and alternate embodiments.

BRIEF DESCRIPTION OF THE DRAWINGS

Preferred and alternate embodiments of this invention is illustrated in the accompanying drawings, in which:

FIG. 7 is a vertical cross-sectional view along the longitudinal direction of pavement showing an illustrated profile having bumps and ridges therein;

FIG. 8 is a vertical transverse cross-section of the pavement showing the location of a rut in the pavement;

FIG. 9 is a plan view of a portion of the pavement illustrating the location, shape and orientation of a crack;

FIG. 10 is a plan view of a section of the pavement illustrating the location and shape of a pothole;

FIG. 11 is a plan view of a portion of the pavement illustrating the shape and orientation of a "D" crack in conjunction with a pavement seam or joint;

FIG. 12 is a plan view of a section of the pavement illustrating the location and configuration of alligator cracks;

FIG. 13 is a vertical cross-section view of the interface of two plates, one being elevationally displaced from the other;

DETAILED DESCRIPTION OF PREFERRED AND ALTERNATE EMBODIMENTS OF THE INVENTION

Figure 2:
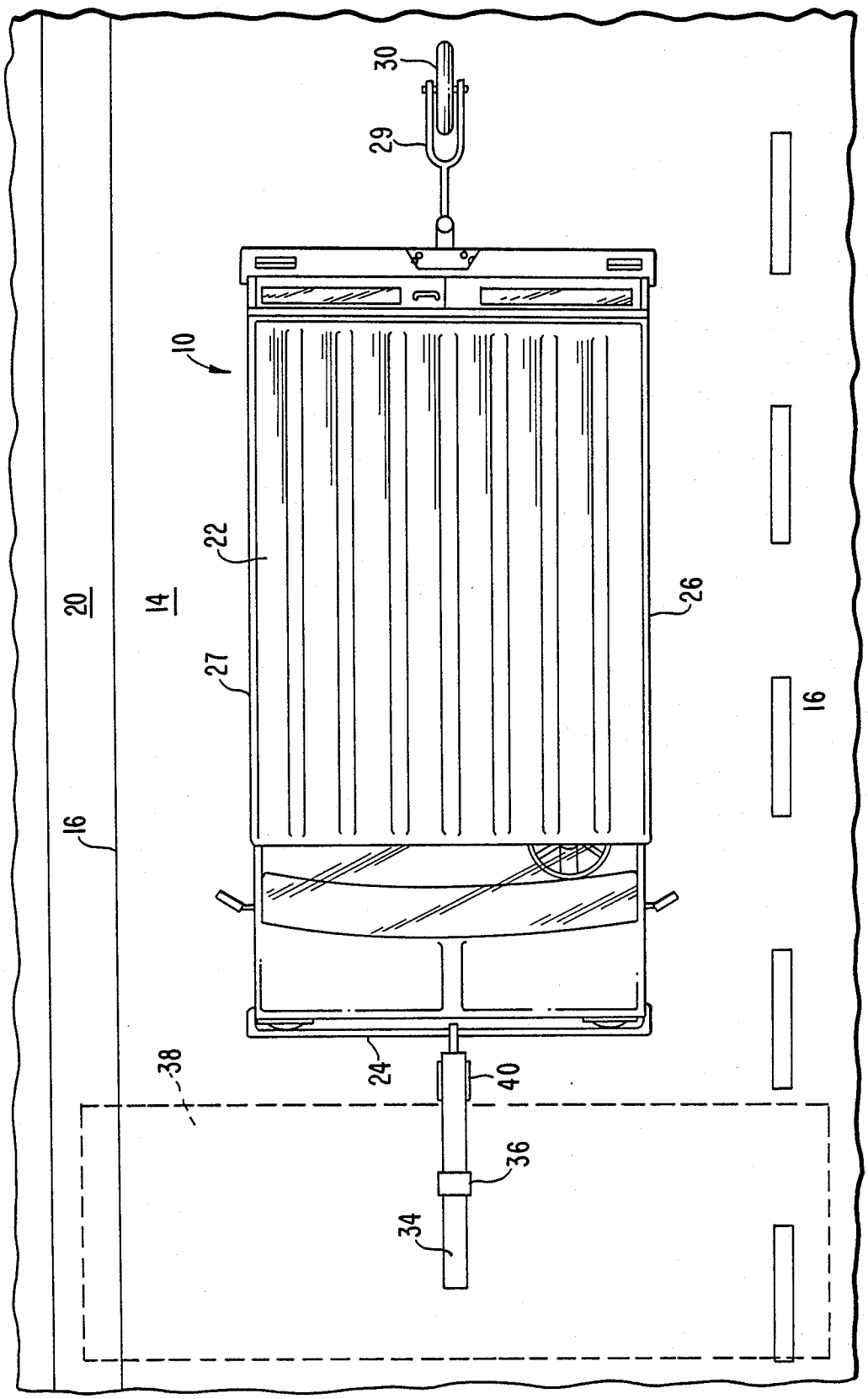
FIG. 2 is a top view of the apparatus illustrated in FIG. 1 showing the position of the cameras, either a video type and/or an infrared type, with respect to the van and illustrating in dotted line a camera field of view of a full width of a lane of the pavement.

The pavement inspection apparatus is generally designated with the numeral 10. The apparatus 10 is designed to inspect a full lane 14 along a selected length of the pavement. The apparatus additionally views a portion of an adjacent lane 16 as illustrated in FIG. 2 and a pavement edge 18 should the lane 14 be the outside lane. A portion of the shoulder or apron 20 is also viewed during the inspection. Most road lanes 14 are 12 feet or less in width. In a preferred embodiment the apparatus is designed to inspect a swath of 13 feet which is in excess of the maximum lane width.

The purpose of the apparatus 10 is to inspect the surface of flexible or rigid pavement 12 to determine the presence and severity of distress features. FIG. 7 illustrates the longitudinal profile of a section of a lane showing humps and dips in the lane.

Additionally the elevational profile of the lane provides information concerning the transverse profile across the lane at selected locations to determine whether or not the lane is worn and has formed rutting along the wheel tracks. A rut is shown in a transverse section in FIG. 8.

Furthermore, the apparatus 10 determines the location and severity of distress features and discontinuities, such as longitudinal cracks, transverse cracks, "D" cracks, alligator cracks, or the like. The presence, severity and frequency of the cracks within a given pavement segment is symptomatic of the condition of the pavement and the sub-surface layered pavement deterioration such as shear displacement, pumping, or the like.

Additionally the apparatus 10 determines the location and severity of potholes or patches, and generally determines the general surface roughness of the pavement by using accelerographs.

VEHICLE

Figure 1:
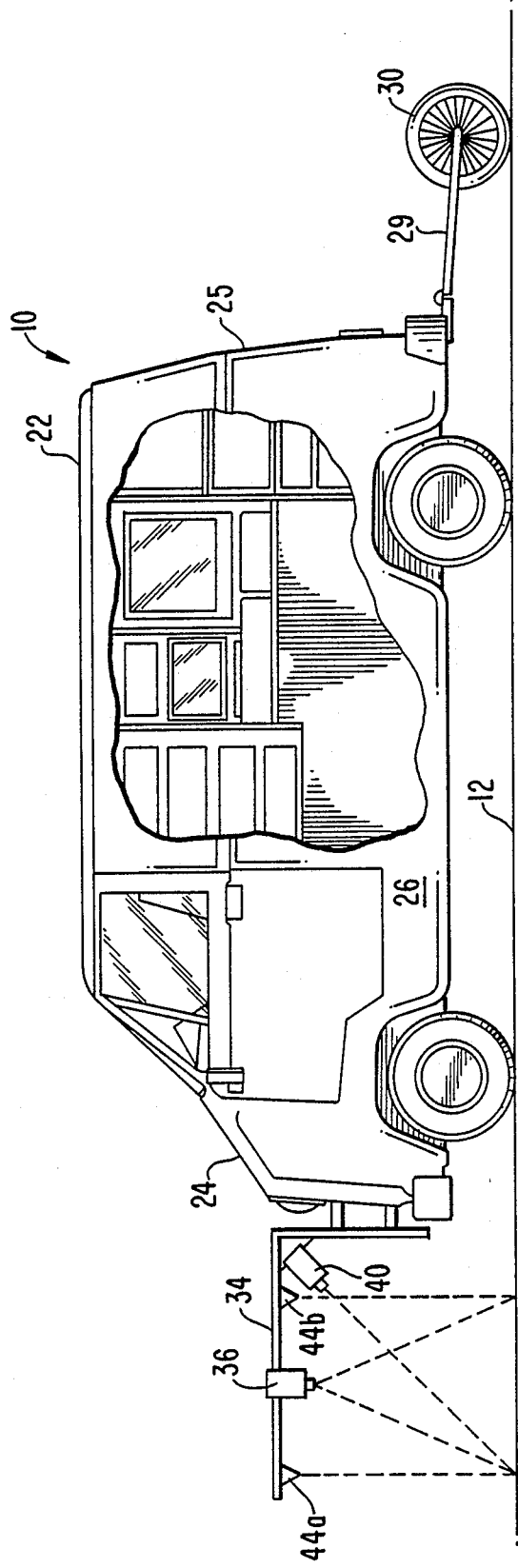
FIG. 1 is a side view of a preferred embodiment of this invention specifically illustrating a wheeled vehicle such as a van having two video array cameras on the van with the cameras projecting towards the pavement at acute angles to each other.

The apparatus 10 includes a self-propelled wheeled vehicle 22 such as a van illustrated in FIG. 1 that is capable of moving down the lane 14 at normal traffic speeds without slowing traffic or causing detours or interfering with normal traffic patterns. The wheeled vehicle has a width of eight feet or less so that no special "wide load" traffic procedures or equipment are required in inspecting the pavement. The vehicle has a front 24, a rear 25 and sides 26 and 27.

The apparatus 10 includes a means for determining the velocity of the van on a real time basis. In a preferred embodiment the velocity determining means includes an odometer unit 29 that is attached to the van for accurately measuring the distance travelled by the van and to pinpoint the location of the pavement currently being inspected. The odometer unit 29 includes an odometer wheel 30 that rotates on the pavement in the lane 14. A transducer (not shown) is associated with the odometer wheel for determining the distance travelled with an accuracy of less than one inch. The apparatus further includes a clock 32 (FIG. 3) (preferably mounted in the van 22) that provides the time of day at which the inspection is taking place and provides lapse time information that is utilized in conjunction with the odometer 29 for determining the velocity of the wheeled vehicle at any particular location.

In an alternate embodiment the velocity may be determined by cross-correlating the frame data from the video array cameras to determine the degree of frame overlap between adjacent frames.

VIDEO ARRAY CAMERAS

The wheeled vehicled 22 further includes a camera support frame 34 that is preferably mounted on the front 24 of the vehicle 22 and projects forward. The frame 34 could alternatively be mounted to the back 25. A first video array camera 36 is mounted on the frame 34 for optically inspecting the lane 14 forward of the vehicle. Preferably the first video array camera 36 projects downward normal to the surface of the pavement 12 and produces a first set of frames of raw electrical video pixel signals or data, concerning or the magnitude of the light radiation reflected by the pavement and received by the camera in an X-Y array (multiple pixel line). In one preferred embodiment, the video array camera 36 is a CCD camera that has high resolution capability for providing electrical video pixel array data in a rectangular field of view 38 indicated by a dotted line in FIG. 2. Preferably the field of view is sufficiently wide to encompass the full width of the lane 14 plus a portion of the adjacent lane 16 and the edge 18 of the pavement and a portion of the shoulder 20. In a preferred embodiment the transverse field of view of the camera 36 is at least thirteen feet and is considerably greater than the width of the vehicle so that at least a full lane of video information can be obtained as the vehicle is propelled down the lane 14.

The apparatus 10 in one embodiment, further includes a second video array camera 40 mounted on the camera support frame 34 for generating a second set of array frames containing electrical video pixel signals or data. The camera 40 is mounted at a fixed distance from and at an acute angle (preferably 45°) to the camera 36 and encompassing a field of view that overlaps with the field of view 38.

Preferably the video cameras 36 and/or 40 are CCD cameras having very high resolutions exceeding 1,000,000 pixels. One particular commercially available video array camera is manufactured by Kodak under the brand name "Megaplus" and has an array of 1,340 pixels in the horizontal direction (X) and 1,037 pixels in the vertical direction (Y) for a total pixel array of 1,389,580.

It is preferable to mount the cameras 36 and/or 40 at a spacing with respect to the pavement 13 so that a single pixel of the camera corresponds to an area on the surface of approximately one-tenth of an inch so that the resolution of the cameras is one-tenth inch/pixel. If desirable, one could utilize a series of laterally spaced cameras in place of a single camera 36 and a series of laterally spaced cameras instead of the single camera 40. In some circumstances it is desirable to utilize a wide angle lens (not shown) with respect to camera 36 and/or 40 to obtain the wide field of view 38 of greater than the width of one lane 14. In the preferred embodiment the field of view 38 extends longitudinally along the lane thirteen feet so that each frame from the cameras 36 and 40 generate surface pixel information from a 13×13 square foot section of the pavement. Video or digital tape recorders 55a and 55b are connected to the encoders 51a and 51b respectively for recording the raw pixel frame data.

INFRARED CAMERAS

As discussed earlier, in order to conduct a sub-surface inspection or exploration of the pavement, infrared cameras are used for capturing the pavement surface temperature profile from the surveillance vehicle 22. The pavement or field heat distortion patterns obtained by the infrared cameras are interpreted by comparing the thermal images to a set of known and/or standard temperature profiles, either laboratory developed or measured, of a best-fit basis or analysis. The standard or know thermal patterns are obtained from, for example, laboratory tests or experiments on laboratory-manufactured concrete, asphalt slabs, concrete slabs, or the like, supported on a variation of known soil layers having known moisture content distribution substantially representing field conditions.

The infra-red cameras can, for example, be the Inframetrics Model 600 type with a 812 micrometer band (Part No. 04418-200), along with a video recorder with standard battery and video tape. The image processor can, for example, be the Inframetrics Thermal Gram I type (Part No. 05215-200).

SURFACE TO PIXEL CALIBRATION

The apparatus 10 further includes a pixel reference means for determining the pixel to surface distance relationship, ratio, or correlation on a real time basis and to adjust or calibrate the raw pixel accordingly. As previously stated the apparatus is designed with an approximate 0.1 of an inch/pixel resolution. However the pixel reference means provides a much more accurate and dynamic (real time) determination of the surface distance to pixel correlation. The pixel reference means counts or measures the number of pixels within a video frame between two mixed or defined reference points and determines if the number varies between frames to maintain a real time correlation of the surface to pixel relationship.

Figure 4:
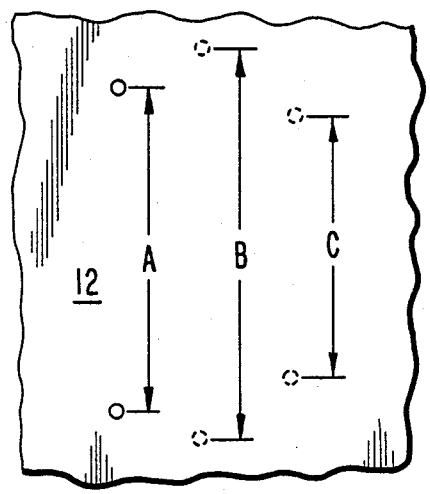
FIG. 4 is a schematic view of a section of the pavement in the view of the cameras showing laser marks formed on the pavement for use as references.

The pixel reference means preferably includes a pair of electromagnetic beam generators such as lasers 44a and 44b that are mounted on the camera support frame 34. The lasers 44a and 44b are spaced a preset precise distance such as four feet and direct parallel laser beams downward onto the pavement 12 within the field of view 38. The beams 44a and 44b form corresponding spots, dots or reference marks on the pavement at precise spaced locations in the field of view of the cameras so that each frame of pixel data contains the distance reference or yardstick. The surface distance to pixel relationship may be initially calibrated when the vehicle is stationary. The marks 46a and 46b are illustrated in FIG. 4. The marks 46a and 46b indicate the dots when the vehicle is stationary in which the cameras are vertically stationary. In this example the distance "A" is exactly four feet. A readout of the cameras 36 and 40 show that there are 480 pixels between marks 46a and 46b. Consequently the surface distance to pixel correlation is initially 0.100 inches/pixel.

During movement of the vehicle down the lane the camera 36 and/or 40 may move up or down depending upon the profile of the pavement. Marks 46c and 46d in FIG. 4 are separated by a distance "B" which indicates an apparent change in the distance between the laser dots due to the vertical downward movement of the cameras. For example, during downward movement the distance "B" may indicate that there are 488 pixels between the marks 46c and 46d. This correlates to a relationship of 0.0984 inches/pixel. When the cameras bounce upward the apparent distance between the dots 46 would be indicated by 46e and 46f being a distance shorter than the reference. For example, the distance "C" may indicate a distance of 472 pixels between marks 46e and 46f. This correlates to a relationship of 0.1017 inches/pixel. Consequently, each frame contains surface to pixel information on a real time basis for adjusting the X-Y reference between the surface distance and the pixel data.

In an alternative embodiment, the reference marks may be established by determining the location of the horizontal pixel rows where the adjacent frames overlap and measure or determine the number of pixels between such horizontal pixel rows.

Figure 3:
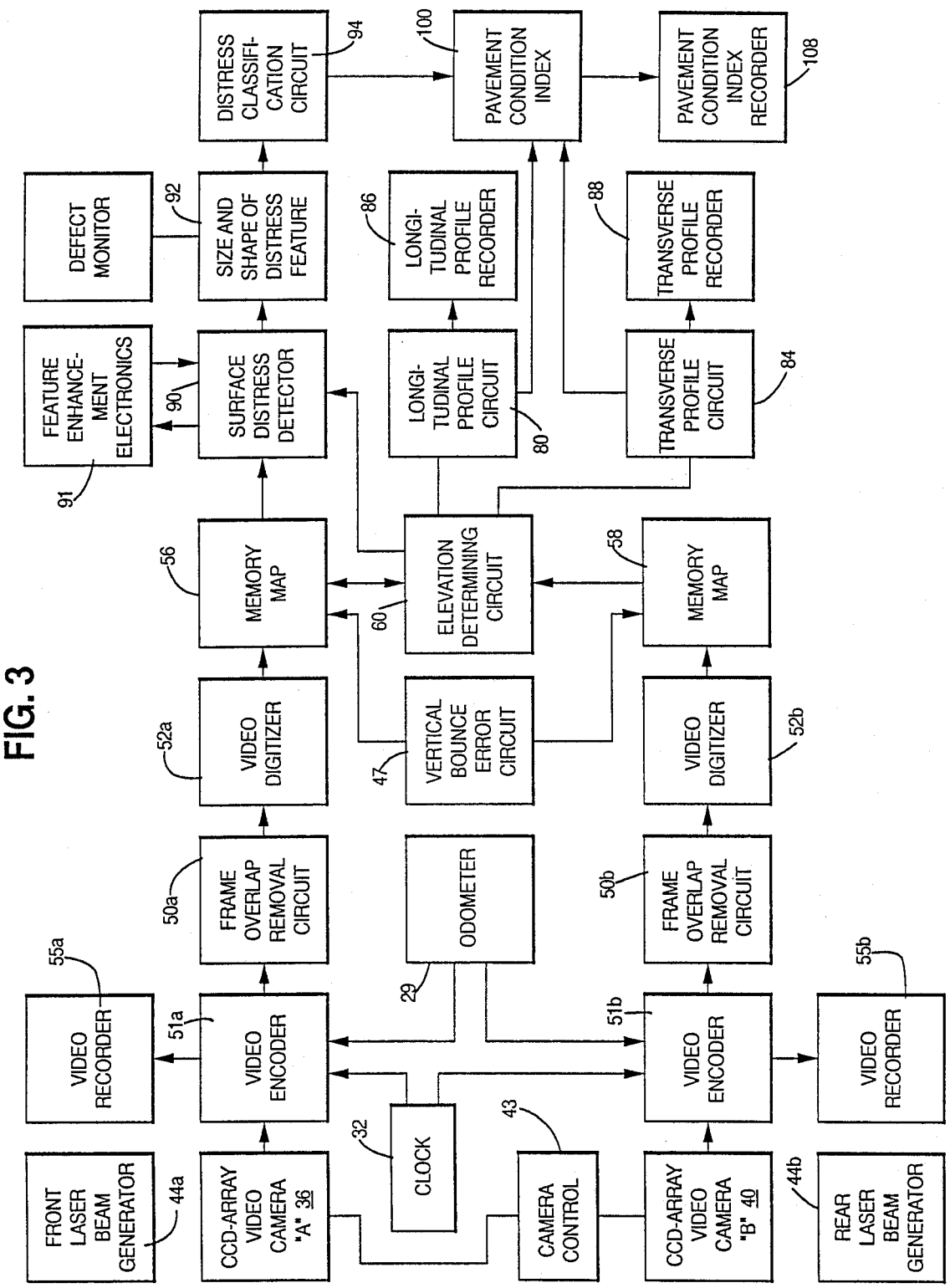
FIG. 3 is a block diagram of the video and electronic components that are a part of the apparatus.

As illustrated in FIG. 3, the apparatus 10 includes a vertical bounce error circuit 47 that looks at each frame or at periodically sampled frames and determines the pixel count within that frame between the reference marks to determine vertical movement of the cameras and accordingly modify the pixel signal information in relationship to the X-Y surface location of each pixel. It should be noted that reference information is contained in each frame enabling very efficient and real time adjustment of the pixel data to the viewed surface distance (area).

The apparatus 10 includes a camera control circuit 48 that is operatively connected to or integral with the cameras for controlling the shutter speed and the frame frequencies. Although both the shutter speed and frame frequencies may depend somewhat upon the nature of the cameras 36 and 40 themselves, it has been found advantageous to utilize a shutter speed and a frame frequency that provides unblurred or geographically undisplaced pixel information at normal traffic speeds such as 55 miles an hour. In this regard, the applicant has found that the camera control circuit 48 is capable of providing a shutter speed of one two-thousandth of a second with the frame intervals or frequencies being 30 frames per second. As previously mentioned each frame contains pixel information representing approximately 13 feet in the longitudinal direction and 13 feet in the transverse direction of the lane 14. The frame frequency may be varied depending upon the speed of the vehicle to minimize the amount of overlap of pixel information that is redundant from one frame to the next as the vehicle travels down the lane. For most cameras, the shutter speed and the frame frequency may be preset.

The apparatus 10 include overlap circuit 50a and 50b that receive the raw electrical video pixel signal information from cameras 36 and 40 respectively and which is responsive to the odometer unit 29 for determining the amount of pixel overlap (redundancy) between adjacent frames. The overlap circuits 50a and 50b remove the redundant electrical pixel signals between adjacent frames so as to present only electrical pixel information that would appear to be continuous ribbon of pixel data as the vehicle moves down the lane.

In an alternative embodiment the overlap electrical pixel signals between adjacent frames are saved for elevational analysis. The overlap electrical pixel signals contain elevational information which may be analyzed to determine the elevational profile of the pavement.

The apparatus 10 includes video encoders 51a and 51b that receive information from the clock 32 and the odometer unit 29 for combining with the pixel information concerning the time of day, position of the vehicle, the velocity of the vehicle and the distance that the vehicle has travelled from a reference point. This information is placed in each frame along with the raw electrical video signals from the cameras 36 and 40.

ELEVATIONAL PROFILE

The analogue electrical video pixel signals are then directed to video digitizers 52a and 52b that convert the analogue signals to digital signals in which each pixel has magnitude words, and X-Y coordinate words and in which the frame includes time, position, velocity and distance information in digitized form.

The apparatus 10 includes memory maps 56 and 58 (RAM) that are operative connected to digitizers 52 and 54 respectively for receiving the digitized frame information and for accumulating multiple frame information to form a memory map containing information with respect to a selected length of pavement such as a segment 100 feet in length. The size of the memory map (selected pavement segment length) may vary considerably depending upon the size of memory desired to be dedicated to this task.

Figure 5:
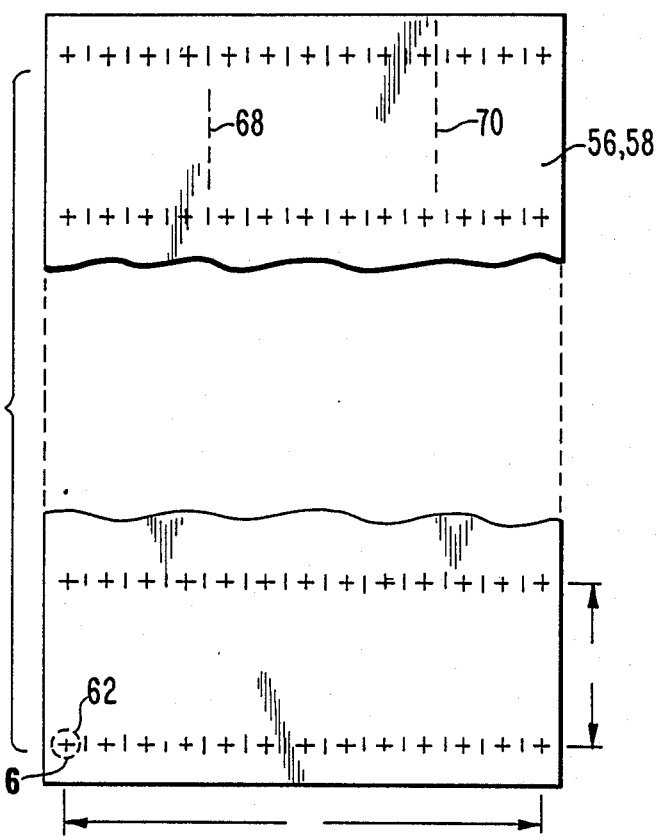
FIG. 5 is a representative section of the pavement in a mass memory showing the location of sampling points for determining the longitudinal and transverse profile of the pavement that is covered by the van.

The memory maps 56 and 58 are usually formed of random access memory (RAM) which is accessible for signal processing to determine the elevational profile of the segment of pavement and to determine whether the segment contains distress features and the severity of the distress features. FIG. 5 is a representation of the memory map showing a section of pavement approximately 13 feet by 100 feet of digitized pixel information. The depicted memory map is a schematic representation of the memory map containing the pixel information.

Figure 6:
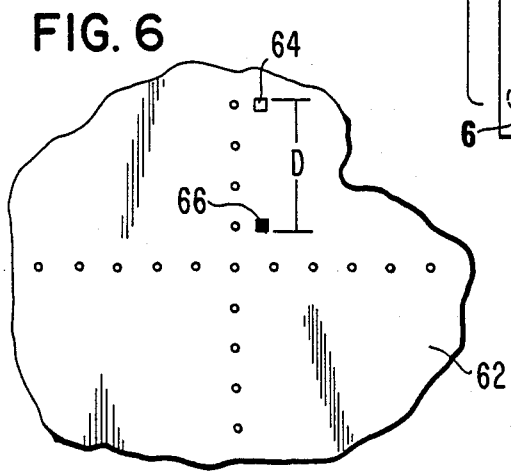
FIG. 6 is a graphic representation of an area of the pavement illustrating the location of pixel elements within the view of the video camera showing different pixel locations of a feature within the view of the two cameras.
Figure 14A:
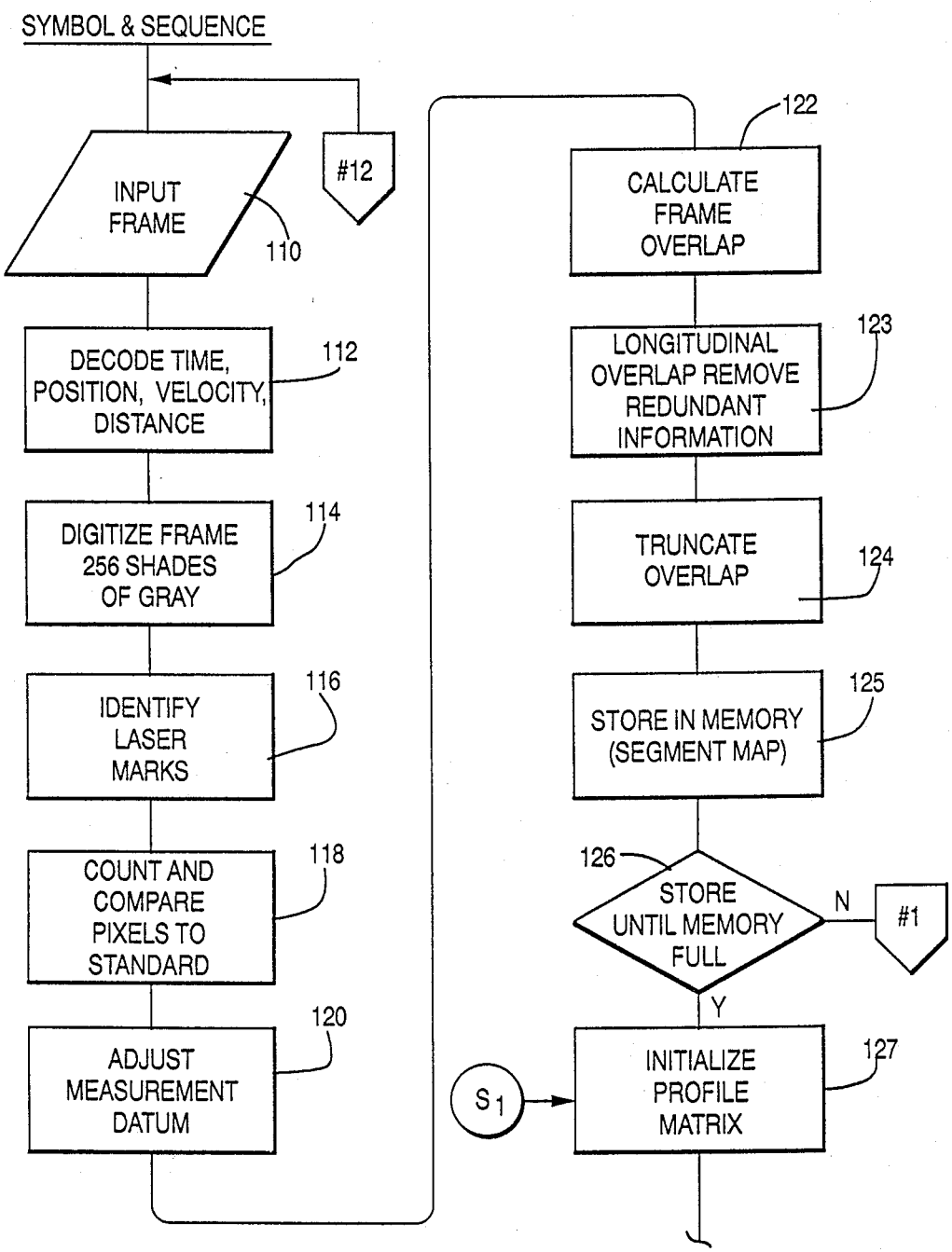
FIGS. 14a–14f are schematic diagrams of a computer flow diagram for the operation of the apparatus.
Figure 14B:
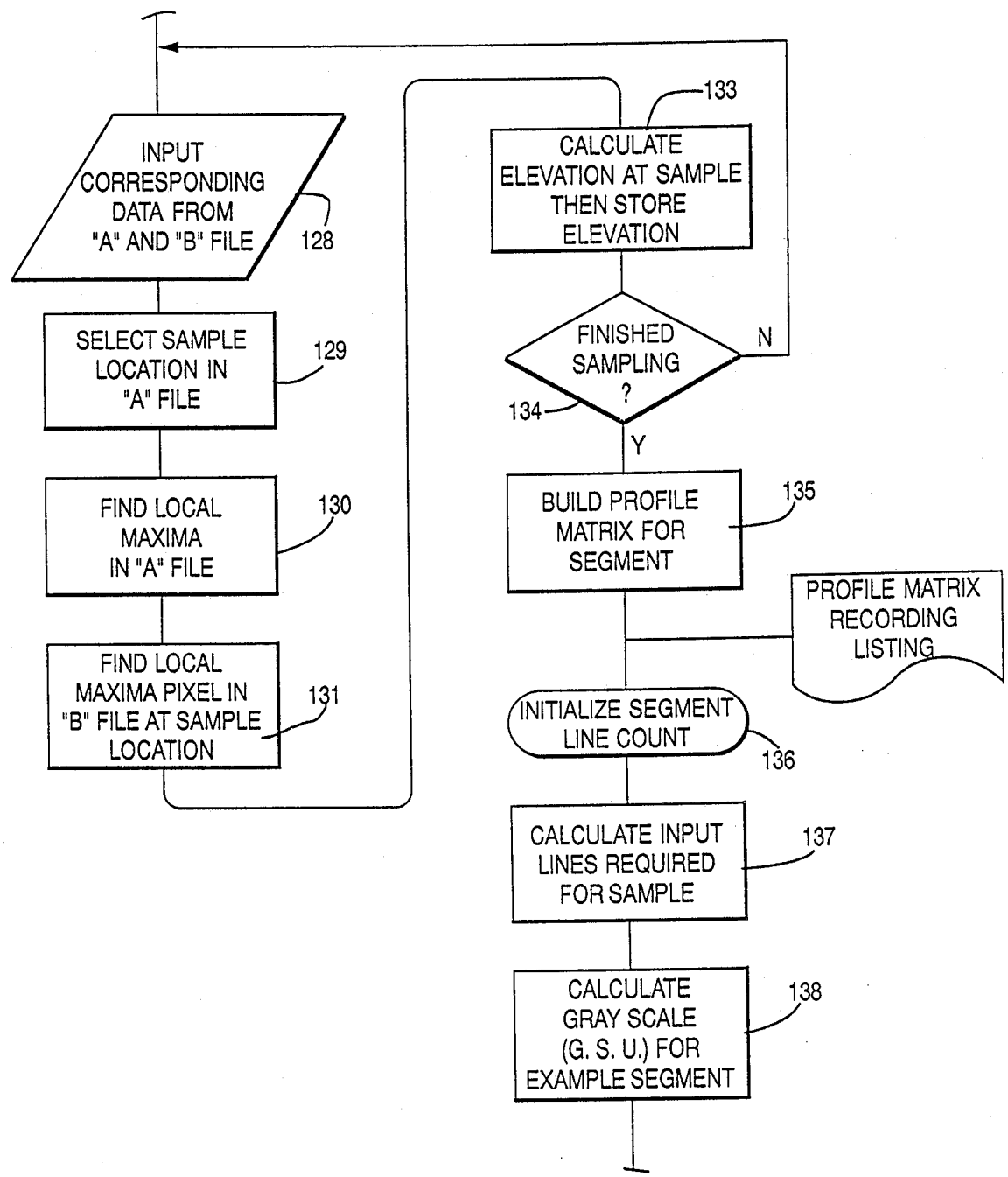
Figure 14C:
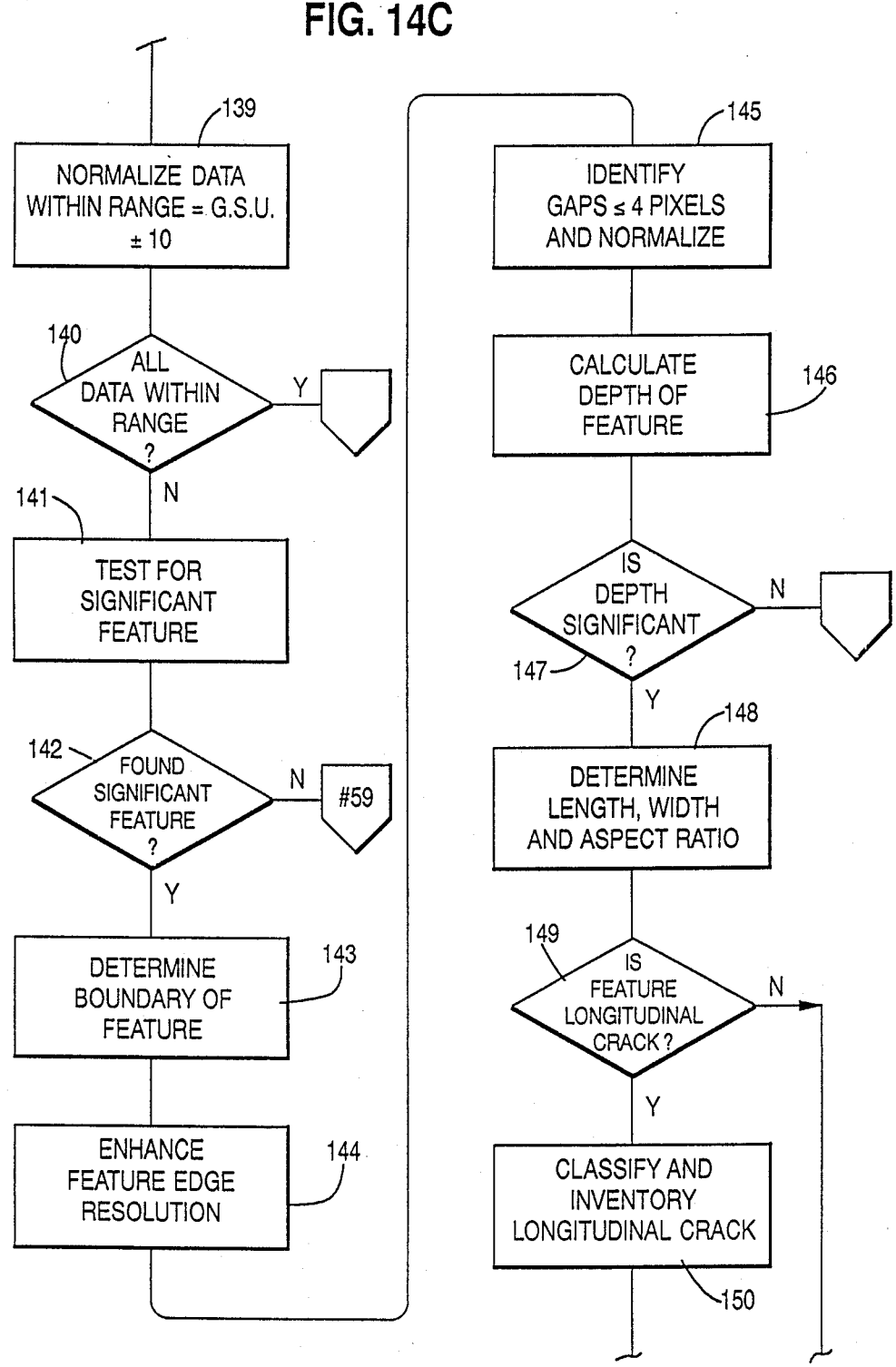
Figure 14D:
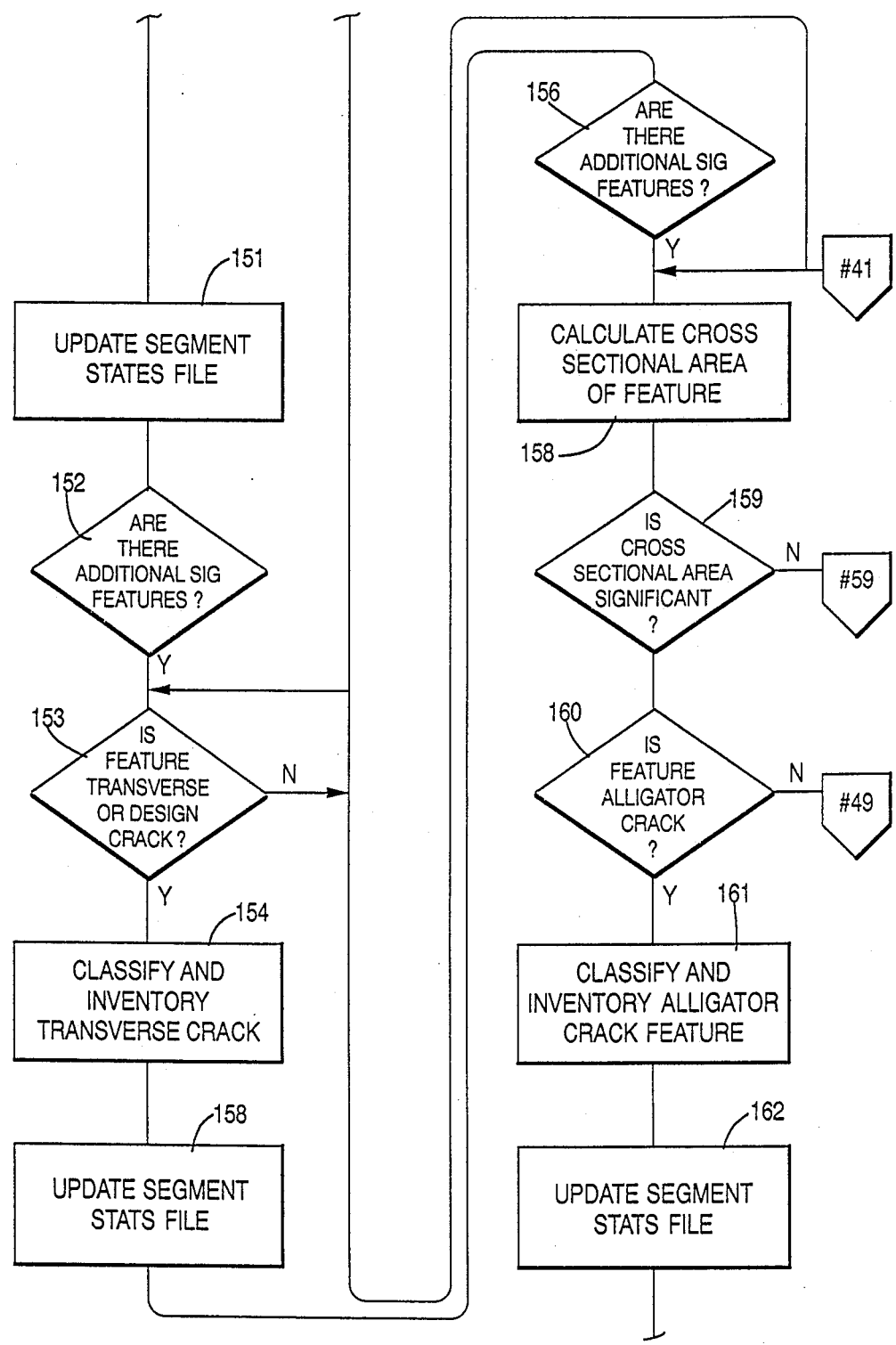
Figure 14E:
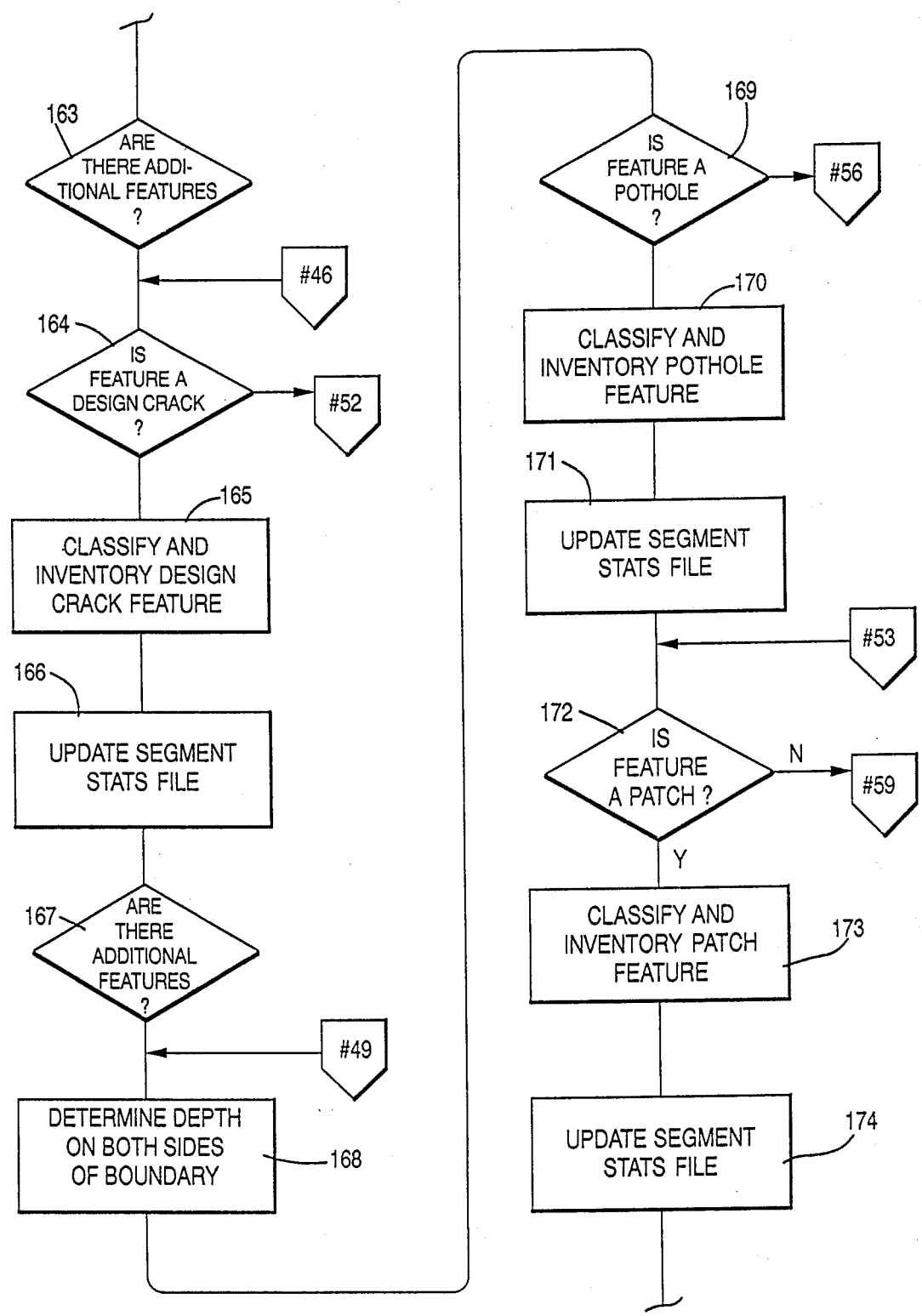
Figure 14F:
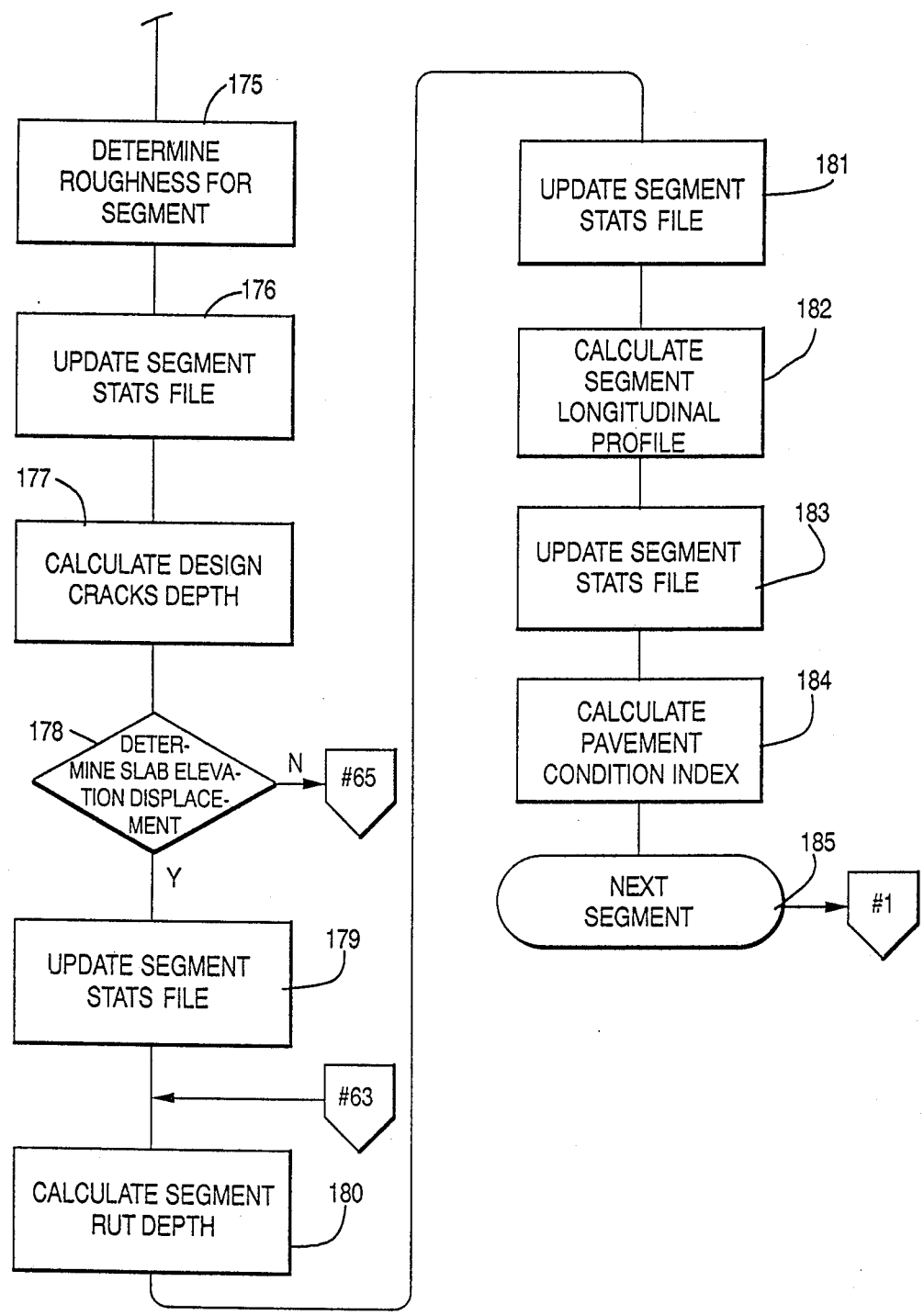

The apparatus 10 has signal processing electronics including a vertical elevation determining circuit means identified with the numeral 60 for comparing pixel information in the two memory maps 56 and 58 to determine the elevational profile of the selected information. After the memory maps 56 and 58 are filled with a first set and a second set of frames of pixel data representing the selected length of pavement segment, the elevational determining circuit compares the pixel data at selected longitudinal and lateral surface areas and determines the elevation of the pavement at the selected locations. The vertical determining circuit means 60 has sample and hold circuits that are preselected to sequentially select only certain areas of the maps to investigate. For example in FIG. 5 there is illustrated a number of sample areas generally designated with the numeral 62 that are spaced both laterally and longitudinally. The elevation determining circuit means 60 analyzes or samples the magnitudes of the pixel data in each of the memory maps in a longitudinal and transverse directions forming a cross within each sample area 62 to determine the X-Y location of the pixel having the maximum value. A frame comparison circuit then compares the X-Y information for each pixel of maximum value of a sample area. The frame comparison circuit determines the X-Y coordinates of the maximum value pixel within the sample area 62 and determines the X-Y distance between the pixels having the maximum values. For purposes of example, a pixel 64 is shown in FIG. 6 as having the maximum amplitude with respect to area 62 in memory map 56. The same sample area of memory map 58 is superimposed indicating the X-Y location of pixel 66 of maximum amplitude for area 62. The frame comparison circuit compares the distance "D" in pixels between the two locations 64 and 66 with the magnitude of the difference "D" representing the elevation of the surface of the pavement at that particular sample area 62 in relation to a reference plane. Consequently the elevation at each sample area 62 throughout the entire pavement segment may be determined by comparing the pixel location of the same surface point in each of the two memory maps 56 and 58. If the two pixel locations 64 and 66 are the same then it would indicate that the sample area is at the same elevation as the reference plane.

As illustrated in FIG. 6, the circuit means 60 samples a multitude of sample areas 62 transversely across the memory maps 56 and 58 respectively at space longitudinal locations. In the example illustrated, the longitudinal spaced intervals are at five feet intervals and the lateral intervals are six inches. Lateral intervals and the longitudinal intervals may be adjusted as desired to obtain the elevational profile resolution desired by the user. In FIG. 5 of memory map 56, wheel tracks 68 and 70 are superimposed thereon to illustrate the lateral intervals across the entire width of the lane including the wheel tracks 68 and 70.

FIG. 7 illustrates a longitudinal profile of pavement 12 in which the elevation of the surface area has been determined by the elevation determining circuit means 60. The pavement is supported on a subgrade layer 74. FIG. 7 shows bumps 76 and dips 77 forming a washboard in the longitudinal profile of the pavement. The results of the frame comparison circuit are processed by a longitudinal profile circuit 80 which compares the results against preset thresholds to determine the degree of elevational deviation from a reference plane to determine the slope of the bumps and dips and the frequency with which the bumps and dips occur and classifies the results in accordance with their severity and frequency within the pavement segment.

For example, if rather small dips and bumps are located at rather close intervals, then it would indicate that the pavement 12 forms a washboard which may indicate a rather severe condition. However if the same size dips and bumps are located randomly at rather large intervals, then the classification may be considerably less severe. If a bump or dip has a rather large magnitude then it may be classified as a very serious surface condition and given a higher priority classification. The classification system may vary depending upon the type of road or highway and upon the criteria used by the maintenance organization. Consequently the frequency and amplitude of the elevational features are compared against preset standards or thresholds to determine a composite quotient for the longitudinal segment of the pavement. Such values determined by the longitudinal profile circuit 80 are recorded by a longitudinal profile recorder 86.

FIG. 8 illustrates a transverse section of the pavement with a rut 82 formed in the right wheel track 70. The apparatus includes a transverse profile circuit 84 that is responsive to the information determined by the frame comparison circuit for evaluating the transverse elevational information with respect to the slope, amplitude and frequency of the elevational information and compares the information against preset thresholds to determine the severity of the elevational information. The depth and width of ruts 82 in the wheel tracks 68 and 70 are very important as an indicator of pavement wear by the traffic. Additionally the rut information is an indicator of the condition and performance of the subgrade layer 74 and its foundation or base. A transverse profile recorder 88 records the information obtained from the transverse profile circuit 84 to record the classification and condition of the pavement as recorded at spaced longitudinal intervals along the pavement and forming a composite picture of the severity of the transverse elevational changes on the surface from one side of the lane to the other side of the lane.

In an alternate embodiment, a single camera 36 is utilized in which the overlap pixel signals are saved and analyzed to determine the elevational profile of the pavement. The overlap pixel signals contain elevational information. Rather than using two cameras, one spaced with respect to the other, the alternate embodiment uses a single camera in which the overlap frame pixel signals represents a view of the same surface from a spaced location and at an inclined angle. Consequently the overlap pixel signals of each frame is analyzed in a similar manner to obtain the elevational profile.

SURFACE DISTRESS FEATURES

The apparatus 10 further includes a surface distress detector circuit 90 that is responsive to the digitized video information stored in memory map 56 (RAM) for determining the presence of surface distress features that exceed preset thresholds. Initially the detector 10 evacuates the information in the memory map 56 to determine if there is any digital information the magnitude of which exceeds a preset "feature" threshold. For example, the detector circuit 90 will determine whether or not there are any magnitude values in the memory map that exceed ±10% from an average of all of the pixel values. A feature enhancement circuit 91 then converts the digitized information to the same value (normalize) for all points that do not exceed the preset deviation value. Unless the magnitude exceeds the threshold it is not considered significant. Such normalization enhances or emphasizes those pixel values that exceed that threshold. The pixel values above the threshold are preliminarily considered features. The surface detection circuit 90 then determines the boundary and X-Y location of the boundaries of the "features" in the memory map 56.

In an alternative embodiment, rather than comparing the pixel values to a magnitude threshold deviation, the pixel values are differentiated by second order differential equations to determine the degree of change between pixel values and to identify features only if there is a rapid change in values, identifying the location of a "sharp edge" of a feature. Such a technique can be referred to as "Laplace" filtering.

The apparatus 10 includes a size, shape and orientation circuit 92 that receives the enhanced information from the surface detector circuit 90 and evaluates the information to determine the size, shape and orientation of each of the surface distress features. If the size of the particular feature is below a certain threshold value, then the feature is classified as a general irregularity or a roughness feature. The size and shape circuit 92 determines the width and length of each of the features and the orientation of the feature and compares the distress feature to preset threshold values to determine if the features are longitudinal cracks, transverse cracks, alligator cracks, D Cracks, potholes, or the like. As illustrated in FIG. 9, the size and shape circuit 92 measures the distance E and F of a particular feature and applies an aspect ratio to determine whether it is a longitudinal or a transverse crack. The size and shape circuit 92 determines the locations of the boundaries or edges 93 of each distress feature.

In FIG. 9, a crack 95 is shown in that its aspect ratio of length to width or width to length is compared to preset thresholds. With respect to the evaluation of alligator cracks 96 (FIG. 12), the proximity of the boundaries with respect to each other and their boundary overlap is determined in its classification. A "D" crack 97 is illustrated in FIG. 11 in which the crack 97 is at the boundary of the pavement with a seam or joint 100.

If a distress feature is determined to be either a pothole 102 or a patch, then the surface defect detector circuit 90 determines the elevation of the pixel information within the boundary to determine whether or not it is a patch or a pothole. In this analysis, elevational information is obtained from comparing the memory maps 56 and 58 as previously discussed.

FIG. 13 illustrates a vertical slab displacement distance G. At every seam or joint in the pavement, analysis is made by the surface defect detector 90 as to the elevation of the slabs on both sides of the joint or seam 100 to determine if there is any vertical displacement. Generally, vertical displacements of slabs on either side of the joint is an indication of abnormal conditions, such as pumping of slabs provoked by the environment, soil, traffic, or the like, of the subgrade and/or foundation.

A distress feature classification circuit 94 then compares the particular values of the distress features against preset severity thresholds to determine their severity. Additionally, the proximity of the distress features with respect to each other is determined to indicate whether or not a particular area of the pavement is more highly distressed than another even though one or more of the features by themselves are not particularly severe.

The data from the defect classification circuit 94 is compiled and analyzed by the pavement condition index circuit 100 to determine the severity and number of surface distress features and their relative proximity within the length of pavement that is represented by the memory maps 56 and 58. This data is correlated and recorded electronically in a pavement condition index recorder 108 as a condition value representing the overall condition of the length of pavement.

Although the digitized pixel information in the memory maps 56 and 58 may be processed using discreet electrical circuits it is preferred to utilize a computer having a mass memory such as a RAM, a program ROM memory, for processing the pixel data utilizing a computer program stored in ROM. A flow diagram of the program is shown schematically in FIG. 14a–14f.

The program consists of a sequence of steps starting with step 110 entitled "input frame" which operates the camera control circuit 48 to obtain a frame of X-Y array pixel data from camera 36 corresponding to the incident electromagnetic radiation from the pavement within the field of view 38. Likewise step 110 inputs the frame pixel data from camera 40. Step 112 takes the output of the sensor from the odometer 29 and the clock 32 and decodes the information and places time, position, velocity and distance information on the frame to identify each frame. Step 114 causes the raw input frame information to be digitized to form digital information representing the magnitude and X-Y coordinates of the incident energy identified with each pixel in the frame. In an eight bit word, 256 different shades of grey may be identified for each pixel.

Step 116 involves analyzing the digitized frame information to locate the high intensity laser reference marks within the frame. In step 118 the distance (in pixel count) between the marks is determined and compared to a standard to determine if there is a deviation from the standard that would indicate vertical movement of the camera. If there is movement in the camera, then the X-Y coordinate pixel information is adjusted to indicate the pixel to pixel center surface distance for that particular frame. Steps 116 and 118 correlate the surface distance with the center-to-center pixel distance to provide a real time continuous calibration. Step 120 involves adjusting the X-Y pixel coordinates in each frame to reflect the real time calibration.

Step 122 involves determining the amount of overlap of redundant pixel information from one frame to the next. Step 122 is responsive to the information from the odometer 29 to determine the degree of overlap between one frame and the adjacent frame in the longitudinal path in the lane. Step 123 provides for the removal of the redundant or overlap information between adjacent frames. Step 124 involves truncating the digitized information in a frame. Step 125 involves storing the truncated pixel data from both cameras 36 and 40 in the memory maps 56 and 58 respectively. Succeeding truncated pixel frames from cameras 36 and 40 are successively stored in the memory maps 56 and 58 respectively until the memory maps are full or until a preset length of pavement has been inspected.

In decision step 126, the process is continued until the memory maps 56 and 58 are full for a particular chosen or selected segment of the lane. In the given example, the information is stored in the memory maps 56 and 58 until a length of approximately 100 feet of pavement frame information has been loaded into the memory maps 56 and 58. In step 127, the memory maps 56 and 58 are initialized to determine the sampling intervals (longitudinal and transverse) to be analyzed to determine the elevational profile of the length of pavement represented in the memory maps. In the example given, the sampling is taken laterally at every six inches across the lane and at every five feet along the longitudinal length of the lane. In step 128, pixel information concerning the corresponding areas 62 from both memory maps 56 and 58 are input from the respective files for comparison in sample and hold circuits. In step 129, a review is made of the magnitudes of the pixels within the sample area 62 of the memory map 56 (camera 36) to determine the location of the pixel having the greatest magnitude in the sample area 62. In step 130, the X-Y location of the pixel with the greatest magnitude is determined.

In step 131, the X-Y location of the greatest magnitude pixel from memory map 58 is determined for the corresponding area. In step 133, the pixel distance "D" between the same surface points as seen by the two cameras, as illustrated in FIG. 6 is determined as representative of the elevation of the area 62 with respect to a reference plane. Steps 128–133 are continued in a loop until the decision has been made in step 134 that the elevation at each of the sampling areas has been determined. Once all of the sampling locations have been analyzed, the information is supplied to the longitudinal profile evaluation circuit and the transverse profile evaluation circuit for determining the slope, frequency, etc., of elevational features within the pavement to determine the severity of the surface profile with respect to preset thresholds. That information then is recorded in the longitudinal profile recorder and the transverse profile recorder to indicate the elevational profile of the pavement.

As indicated in step 135, a profile matrix of the segment of the pavement is made through the longitudinal profile evaluation circuit and the transverse profile evaluation circuit with the information being recorded in the profile matrix recorders.

In summary, steps 127 through 135 determine the elevational profile of the lane of pavement being investigated. In step 133, the information is calculated with respect to the difference between the location of the pixel in the two memory map in relationship to the projected angle of camera 40 with respect to camera 36. It should be understood that the sampling resolution may vary depending upon the users desires. If higher resolution information is desired, then the intervals between the sampling areas may be less. However, if lower resolution is acceptable, then the distances between the sampling areas may be increased. In step 135, each segment of pavement has a profile matrix created that is stored.

Starting with step 136, the program initializes the beginning pixel line of each pavement represented in the memory map 56 to have a reference location for determining the location of surface distress features. In step 136, the memory map 56 is broken up into sections so that distinct distress features may be determined for each particular section. In one example, one may want to look at the distress features in a section that measures four feet in the longitudinal direction and thirteen feet in the transverse direction. Consequently in step 137 the number of pixel lines constituting a four foot longitudinal section is determined.

In step 138, a calculation is made concerning the mean and range of gray-scale values of the pixels within that thirteen feet by four feet sample segment. In step 139, the gray-scale values of each of the pixels within the segment are evaluated to see how close they are to the mean value. If they are within a preset percentage deviation (threshold) then the values are set at the mean value (normalized). In decision step 140, it is determined whether or not all of the pixel values fall within the range. If they do, it is determined that there are no significant surface distress features within that segment and the program then proceeds to look at the next adjacent segment. If it is determined in the decision step 140 that not all of the pixel values fall within the range, then one proceeds to step 141.

In step 141, it is determined whether any significant distress features are located in the section. In step 141, the number of contiguous feature pixels is compared to a preset value to initially determine feature area size. For example, if there are forty or more contiguous pixels that exceed the threshold value, then a decision is made that there is a significant feature within the section. If there are less than forty contiguous pixels, then this fact is recorded as surface roughness and that is recorded as a distress feature, usually of lesser significance. Step 142 is a decision step that a significant feature (greater than 40 contiguous pixels) was found. In step 143, an evaluation is made to determine the X-Y locations of the boundaries of the found feature. In step 144, the pixels adjacent to the boundary are reevaluated with respect to the original values within a much closer tolerance such as a ±5% to determine a more precise location of the boundaries and to enhance the boundary or edge resolution of the feature. In step 144, the pixel information is normalized by interconnecting discontinuities in adjacent pixels if the discontinuity is less than a certain number of pixels. For example, if there is a gap of less than four pixels, then that is determined to be a insignificant gap and the values of the pixels in the gap are set to a value corresponding to the boundary so as to normalize the information and to enhance the boundary identification. If the gap is greater than four pixels, then it is determined that the feature is an adjacent distress feature which will be analyzed separately. In step 146, the elevation of the area within the boundary of the feature is determined utilizing the process in step 128 through 133 to determine the depth of the distress feature. The depth values of pixels within the boundary of the distress feature are compared to preset values to determine if the depth of the feature is significant. For example, if the depth range is ±10% then it is determined that it is not insignificant.

If the depth of the distress feature is significant as determined in step 147, then the program proceeds to step 148 to determine the length, width and aspect ratio of the distress feature. The aspect ratio is the ratio of the length to the width. After such information is obtained, the process proceeds to step 149 which evaluates the information to determine whether or not the feature is significant and whether it is a longitudinal crack. To be a longitudinal crack, the length is evaluated with respect to a minimum crack length and width to determine whether the crack is significant or should be ignored. For example, in a preferred embodiment, the minimum threshold indicates that the length of the feature should be at least 12 inches long. If the aspect ratio is greater than a certain value, then it is classified as a longitudinal crack. For example, in the preferred embodiment if the aspect ratio of the length to the width is greater than 8, then it is determined to be a longitudinal crack and is classified and inventoried as such in step 150.

In step 150, the severity of the longitudinal crack is also determined by comparing the dimensions to certain threshold values, usually established by a government agency responsible for maintaining the pavement. For example, if the width of the crack is less than one-half inch, then it is classified as a minor Class I longitudinal crack. If the crack has a width between one-half and two inches it is classified as an intermediate or Class II crack. If the longitudinal crack has a width greater than two inches, then it is classified as a major or Class III crack. In step 151, the information is placed in a pavement section file concerning distress features relating for that section. It is noted, however, that a crack close to one-half inch will result in structural failure; thus a crack of this size is significant. It is also noted generally that crack width is related to the load-transfer capability of the pavement. In other words, the above-described massive cracks essentially depict an already failed pavement.

In decision step 152, it is determined whether or not the previous feature was the only feature in the segment or whether there are still significant remaining features. If the additional feature is not a longitudinal crack then the program proceeds to the decision of whether the feature is a transverse or design crack in step 153. In step 153, the aspect ratio is compared against a threshold value such as 0.125. To be significant the feature must have minimum length of six inches to be classified as a transverse crack. In step 154 the transverse crack is classified with respect to severity into a number of classifications. Generally, however, transverse cracks are temperature cracks which extend the entire width of the pavement; e.g., through a transverse joint. In step 155, such information is loaded into the statistical file for that segment and the process is repeated to determine if there are any other significant features.

If none of the other features fall within the categories of transverse or longitudinal cracks, then in step 157 the feature is evaluated with respect to its cross-sectional area. In decision step 159, the area of the feature is compared against a cross-sectional area threshold to determine whether the feature is significant. For example if the cross-sectional area is greater than two and one-half inches it is determined that it is a significant distress feature.

Then, program step 160 determines whether it is an alligator crack by looking at the adjacent areas to determine whether there are three or more polygons that are adjacent to each other. If there is not, then the feature is further analyzed in subsequent steps. For example, if the area is less than a certain value, then it may be classified as a minimum alligator crack. If it falls within a certain intermediate evaluation it is determined as an intermediate crack, and if it exceeds a higher value then it may be determined as being a severe or major alligator crack. It is noted that the severity of the alligator cracks is relative to the deterioration of the pavement foundation's material. Such information then is updated in the file for that segment in step 162.

Then, in step 163, the question is asked whether there are additional features in the segment. If there are, then they are analyzed accordingly to determine whether or not they are a transverse crack, longitudinal crack, alligator crack and the like. In step 164 a measurement is made to see if the feature is a design or "D" (as illustrated in FIG. 11) crack in which one of the boundaries of the feature is a seam or expansion joint. If it is determined to be a design crack, then it is classified as such in step 165. Information is placed in the statistical file in step 166.

In decision step 167, the question is asked whether there are any other additional features. If there are, then a determination is made with respect to the depth of the feature on both sides of the boundary to determine whether it may be a pothole or a patch. If the elevation drop is greater than 30% within the feature as compared to the area outside the boundary, then it is indicative of a pothole as determined in step 169. The severity of the pothole is classified and inventoried in step 170; and updated and placed in the statistical file for the segment in step 171.

If the elevation does not indicate that the feature is a pothole then it is evaluated to see if the pixel information within the boundary indicates it is an elevation rise of greater than a certain threshold, such as 15%; indicating that it is a maintenance patch. This determination is made in step 172. If it is determined to be a patch, then the severity of the patch, particularly size, is determined in step 173 and classified in the statistical file and inventories in step 174.

In previous evaluations, if it was not determined to be significant if was generally classified as a possible roughness. In step 175, the physical size of the unclassified other or miscellaneous features are determined in step 176 and placed in an appropriate statistical file as general roughness for that segment.

An additional calculation is made if design cracks are identified to determine whether there is a slab elevational change on either sides of the seam or joint indicative of slab displacement or pavement separation. In step 176, depth measurements are made concerning the elevation of the slabs on both sides of the joint. The information is value rated in step 178 to determine whether or not there is significant slab displacement. If it is, the information is placed into the statistical file for the section in step 179.

In a preferred embodiment, it is desirable to compute the absolute value and the rate of change of the rut depth in the longitudinal direction in the wheel track 70. Thus in step 180 the rut depth is calculated in the longitudinal direction separate and apart from the general profile elevations. The rut depths are calculated using the techniques of steps 127–135. Calculations are made of rut depth with respect to its mean value, range and standard deviation over the wheel track for each segment. The rut depth information is stored in step 181. Like calculations are made in steps 182 and 183 with respect to the general longitudinal profile.

In step 184, a general pavement condition index for the entire pavement segment is calculated by combining all of the information concerning the transverse profile, the longitudinal profile and the surface distress features. The variables and the weight given to each of the variables to be calculated in the pavement condition index may vary from user to user. However, the index is usually a summary indication of the general condition of the segment that has been investigated. In step 185 the program returns to the beginning and looks at the next segment along the length of the pavement for the particular lane being driven.

Figure 15A:
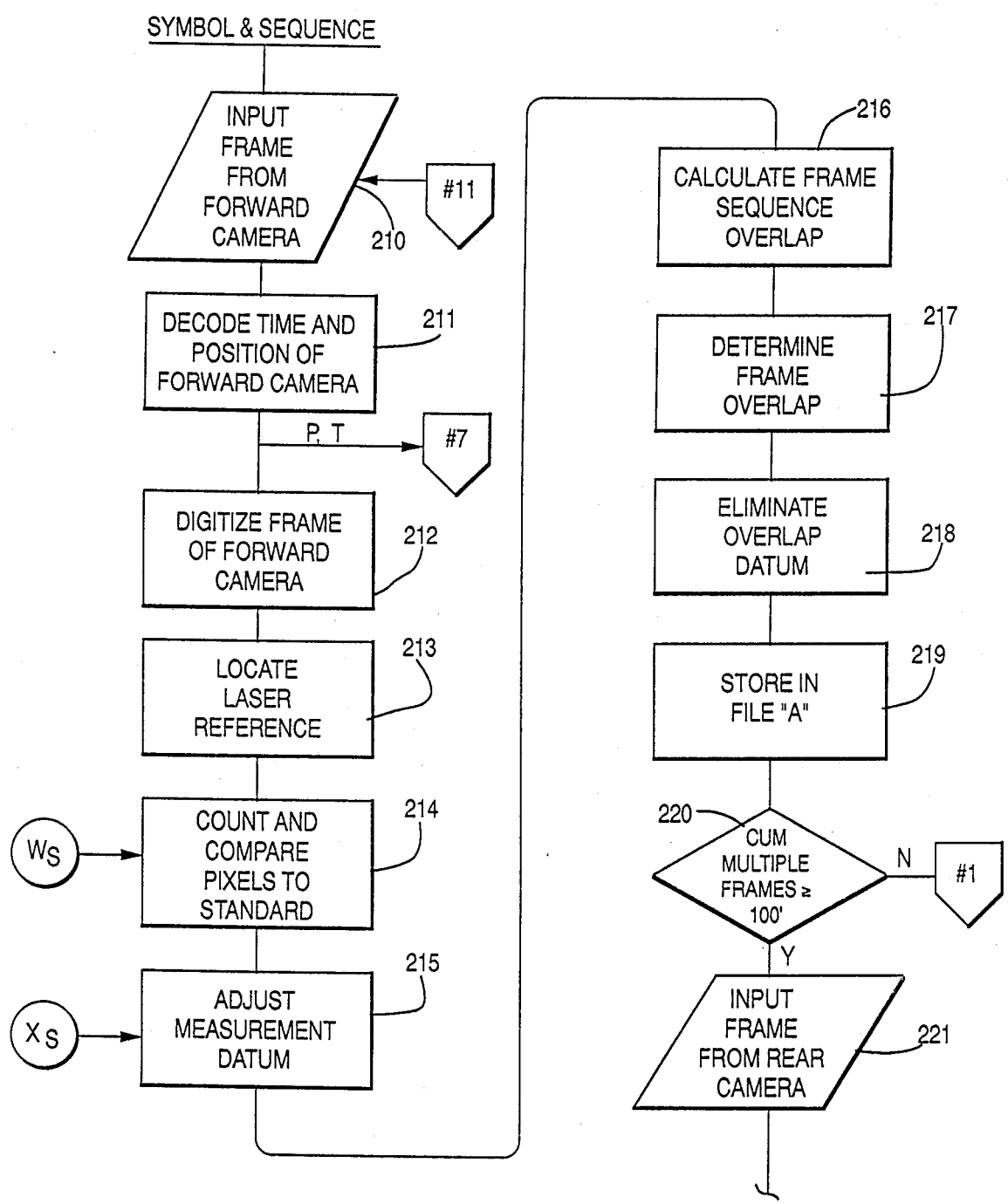
FIGS. 15a–b are schematic diagrams of a flow diagram of a computer program for operating equipment.
Figure 15B:
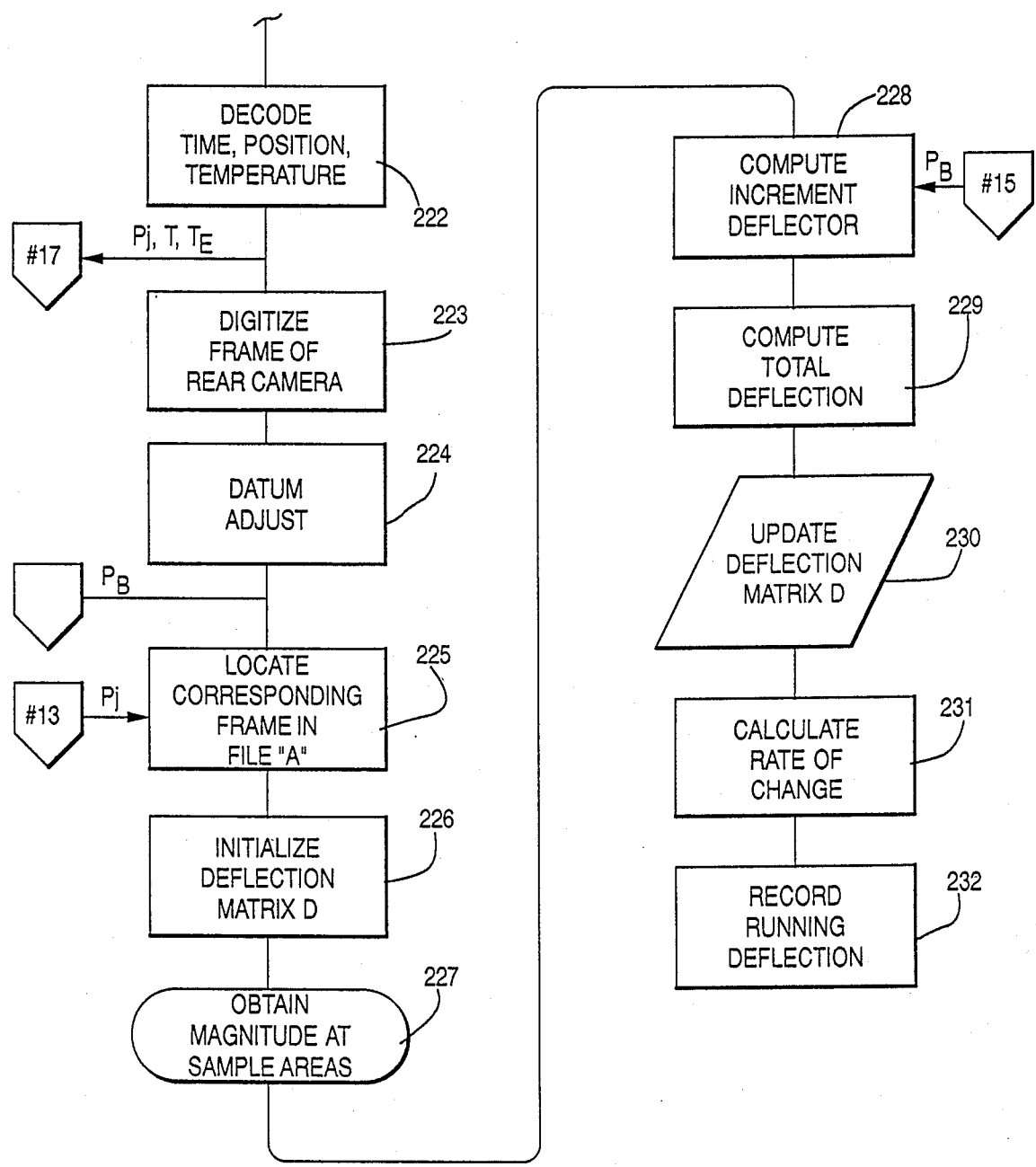

Preferably, the information is processed utilizing a computer with (1) a CPU, (2) mass data storage (RAM) and (3) a program stored in ROM. A flow diagram of a sample computer program is illustrated in FIGS. 15a–b.

Step 210 inputs the frame information from the forward camera 192. For example in a preferred embodiment, the frame information would correspond to the right rut and include information from a swath that was three feet long and five feet wide for each frame. Information from the odometer 29 and the clock 32 is combined with the pixel data in step 211 so that each frame has identifying information as to time, position, distance and velocity. The frame information then is digitized in step 212.

In steps 213 and 214, the pixel distances between the laser references marks are measured to correlate the pixel X-Y coordinates with the pavement surface being viewed by the camera 192. If there is a deviation from the standard value then the frame pixel data is adjusted in step 215.

In steps 216–218, the amount of adjacent frame overlap of redundant pixel data is determined and removed from the frames in response to information from the odometer 29. The remaining, nonredundant pixel information is then stored in a memory file or map such as RAM in step 219. The frame pixel data will be sequentially stored in the memory map until the map is full or until a preset length of pavement has been viewed. For example, it may be desirable to accumulate information for a pavement segment of up to 100 feet in length in which each recorded segment or portion is three feet wide and five feet long. Consequently in step 220, the memory map is successively loaded with the frame pixel data until the full 100 length of information had been obtained (first set of frames).

In step 221, the pixel data from the rear camera 196 is received in which each frame is identified with time, position and pavement temperature information along with the pixel data from the camera 196. The frame data then is digitized in step 223. In step 224, the information is adjusted depending upon the vertical movement of the camera 196 as previously discussed in similar steps 213-215. In step 225, location and values of pixel data from the first set of frames of the forward camera 192 corresponding to the sample points 200a-g is retrieved and used as a comparison reference as an indication of the values of the undeflected pavement of the sample points. Step 226 is quite important since it initializes the X-Y location of each sample point in the frames from the rear camera 196. In step 227, the pixel magnitude information at each of the sampling points is obtained.

In step 22B, the incremental vertical displacement at each sample point. In step 230, the pavement deflection information is added to a common file to provide pavement deflection values at selected intervals along the lane. In step 231 calculations are made concerning the incremental change of the values in relationship to the distance to determine the rate of change of the deflection along the road which is indicative of changes in the quality of the road bed itself. In step 232, such information is recorded for each segment of pavement.

Although not shown, the apparatus includes lighting for artificially illuminating the field of views of the cameras 36, 40, 192 and 196 to enable the apparatus to be utilized at anytime during the day and to minimize the effects of shadowing.

Upon reviewing the foregoing material it can be appreciated that the apparatus 10 is very versatile and is capable of being operated during normal traffic times and a normal traffic speeds without disrupting normal traffic flow and requiring the use of unusual procedures such as "wide load" procedures. The system is capable of obtaining information concerning the condition of the pavement at a very reasonable cost per mile. Furthermore, the amount of time required to inspect long segments of pavement is greatly reduced, providing pavement engineers with more accurate information in a shorter period of time.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

While the invention has been particularly shown and described in referenced to preferred embodiments thereof, it will be understood by those skilled in the art that changes in form and details may be made therein without departing from the spirit and scope of the invention.

I claim:

1. A pavement distress survey system comprising:
a surface vehicle means for moving over a length of a pavement being inspected;
a first video camera means for optically inspecting said pavement for surface defects, wherein said first video camera means is mounted on said surface vehicle means and is projected towards said pavement, and wherein said first video camera means moves over a surface of said pavement as said surface vehicle means is moved over said length of said pavement;
a second video camera means for optically inspecting said pavement for surface defects, wherein said second video camera means is mounted on said surface vehicle means spaced apart from said first video camera means and is projected onto said pavement surface at a generally acute angle relative to said first video camera means for having a second field of view which has at least a portion thereof in common with said first video camera means; and
a video signal processing means for determining a surface condition of said length of said pavement travelled by said surface vehicle means, wherein said video signal processing means is operatively connected to said first and second video camera means,
wherein said first and second video camera means comprise infrared video camera means for capturing the pavement surface temperature profile from said surface vehicle means.

2. The pavement distress survey system as in claim 1, wherein said infrared camera means obtain pavement or field heat distortion patterns.

3. The pavement distress survey system as in claim 1, further comprises comparing means for comparing thermal images of said pavement or field heat distortion patterns obtained by said infrared cameras to a set of known and/or standard temperature profiles.

4. A method of detecting and identifying pavement distress features, comprising the steps of:
providing a surface vehicle means for moving over a length of pavement being inspected;
optically inspecting said pavement at a given first angle for surface defects over a surface of said pavement for having a first field of view as said surface vehicle means is moved over said length of said pavement;
providing first output data;
optically inspecting said pavement at a second given angle for surface defects for having a second field of view which has at least a portion thereof in common with said first field of view;
providing second output data; and thereafter
determining a surface condition of said length of said pavement travelled by said surface vehicle means,
wherein said steps of optically inspecting said pavement at given first and second angles comprises the steps of optically inspecting said pavement with first and second infrared cameras, respectively.

5. The method of detecting and identifying pavement distress features as in claim 4, wherein said steps of optically inspecting said pavement with first and second infrared cameras comprise the steps of obtaining pavement or field heat distortion patterns.

6. The method of detecting and identifying pavement distress features as in claim 5, further comprising the step of comparing thermal images of said pavement or field heat distortion patterns obtained by said infrared cameras to a set of known and/or standard temperature profiles.

7. A pavement subsurface exploration system, comprising:
- a surface vehicle means for traversing along said pavement;
- a first infra-red camera means for thermally inspecting said pavement for subsurface moisture distribution and soil characteristics, wherein said first infra-red camera means is mounted on said surface vehicle means, and is projected towards said pavement;
- a second infra-red camera means for thermally inspecting said pavement for subsurface moisture distribution and soil characteristics, wherein said second infra-red camera means is mounted on said surface vehicle means and spaced apart from said first infra-red camera means, and is projected towards said pavement; and
- a video signal image processing means for determining the surface temperature profile of said pavement travelled by said surface vehicle means.

8. The pavement subsurface exploration system as in claim 7, wherein said first infra-red camera means moves over a surface portion of said pavement as said surface vehicle means moves along the length of said pavement.

9. The pavement subsurface exploration system as in claim 7, wherein said first and second infra-red camera are projected on said pavement for full coverage of the width of said pavement.

* * * * *